United States Patent

Spiesel

[11] Patent Number: 5,997,847
[45] Date of Patent: Dec. 7, 1999

[54] ECTOPARASITE DETECTION METHOD

[76] Inventor: Sydney Z. Spiesel, 77 Everit St., New Haven, Conn. 06511

[21] Appl. No.: 09/004,121

[22] Filed: Jan. 7, 1998

[51] Int. Cl.[6] ............................ G01N 33/52; A61K 49/00
[52] U.S. Cl. ............................ 424/9.6; 424/9.1; 424/9.8; 435/7.1; 436/501; 436/172; 436/811; 436/815; 514/881
[58] Field of Search ...................... 436/172, 501, 436/63, 800, 811, 815; 435/7.1, 287.1, 29, 34; 424/9.1, 9.6, 9.8; 514/65, 881

[56] References Cited

U.S. PATENT DOCUMENTS

| 3,625,904 | 12/1971 | Nosler et al. |
| 5,353,803 | 10/1994 | Cerra. |
| 5,547,665 | 8/1996 | Upton ............................ 424/94.61 |
| 5,658,750 | 8/1997 | Sheftel et al. ............................ 435/29 |

Primary Examiner—Christopher L. Chin
Assistant Examiner—James L. Grun
Attorney, Agent, or Firm—Alix, Yale & Ristas, LLP

[57] ABSTRACT

A method of detecting the infestation of a host by arthropod ectoparasites uses a fluorescent dye which stains the ectoparasites and/or their eggs but not the adjacent skin or hair to which they are attached. The dye can be incorporated into a shampoo or a rinsing solution and is applied to the scalp or other region of the host. After a suitable period of time has elapsed, the dye-containing solution or shampoo is rinsed off and the hair and adjacent area of the host examined under ultraviolet or near-ultraviolet light. Such illumination will cause the stained ectoparasites and/or eggs to glow and, thus, become easily detectable for diagnosis and subsequent removal. The method may be applied to detect scabies (i.e. skin-burrowing mites), head lice, body and pubic lice and to any other arthropod ectoparasites and their eggs containing a substantial percentage of chitin.

18 Claims, 1 Drawing Sheet ated with a cobalt blue filter. Such
illumination will cause the stained ectoparasites and/or eggs
ECTOPARASITE DETECTION METHOD

BACKGROUND OF THE INVENTION

1. Field of the Invention

The present invention generally relates to the field of ectoparasite detection. More particularly, the invention relates to methods and apparatus for the detection of arthropod ectoparasites and their eggs which have infested live hosts such as humans or other animals. Accordingly, the general objects of the present invention are to provide novel and improved methods and apparatus of such character.

2. Description of the Related Art

Arthropod ectoparasite infestation is an enormously persistent and troubling condition today even in industrialized nations. For example, pediculosis capitis or head lice infestation presently afflicts an estimated 12 million patients or hosts in the United States alone. Most of these hosts are school children. These arthropod ectoparasites are easily spread from child to child and are hard to eliminate once the host child has been infested. The lice themselves, which generally remain at or near scalp level, are small and difficult to find. Naturally, once infestation has begun in a host, the condition persists and is exacerbated by the reproductive cycle of the lice. Thus, the lice produce eggs, or nits, which are tenaciously affixed near the bottom of the hair shafts by a cement produced by female lice. Given this, it has long been recognized that the key to pediculosis diagnosis and treatment lies in the detection and removal of nits.

In early days, control of this parasite was accomplished by a variety of wholly manual treatments. For example, lice detection and removal has long been effected by laboriously searching the scalp of an infested host and hand-removing individual louse eggs, or nits, attached to the hairs of the host. Painful and slow combing with a fine-tooth comb has also been commonly used to remove nits. This method is generally considered to be a slightly faster and more effective variant of the hand-removal method. Other methods of nit and/or louse removal include shaving the scalp or soaking the hair and scalp with dangerous materials such as kerosene. More recently, efforts have concentrated on developing chemical pediculicides to treat lice infestation. One significant drawback of such pediculicides is that evolutionary selective pressures inevitably give rise to strains of head lice which are resistant to the pediculicides. Thus, newly developed pediculicides rapidly lose effectiveness. Accordingly, removal of nits by hand or with a fine-tooth comb remains the most effective method of removing head lice. Since nits are generally less than a millimeter in diameter, they are quite hard to detect, especially in children with thick, fine hair. Thus, it is still common for a thorough delousing of the scalp using a fine-tooth comb to require over one and one half hours. Further, this combing process often needs to be repeated daily because it is so easy to overlook nits.

Therefore, there remains a need in the art for an improved method of detecting arthropod ectoparasite infestations which overcomes the aforementioned deficiencies of the related art by providing a rapid, sensitive and accurate diagnostic method that provides initial, early and yet definitive diagnosis of infestation.

Further, there remains a need in the art for an improved method of detecting arthropod ectoparasite infestations which overcomes the aforementioned deficiencies of the related art by providing a method of detecting such infestations which enables advantageous treatment without the need for costly and dangerous chemical insecticide and acaricide treatments.

SUMMARY OF THE INVENTION

It is, accordingly, an object of the present invention to provide an arthropod ectoparasite detection method which provides rapid, sensitive and accurate diagnostic methods for early and definitive diagnosis of arthropod ectoparasite infestation.

It is a further object of the present invention to provide a safe and cost-effective method of detecting arthropod ectoparasites which enables advantageous treatment without the need for costly and dangerous chemical insecticide and acaricide treatments.

It is still another object of the present invention to provide an improved method of detecting arthropod ectoparasites which provides an optimal combination of (1) simplicity; (2) accuracy; and (3) economy.

These and other objects and advantages of the present invention are provided in one embodiment by a method of detecting arthropod ectoparasite infestation by the use of a fluorescent dye which stains ectoparasites and/or their eggs but not the adjacent skin or hair of the host to which they are attached. The dye can be any one of a wide variety of dyes which self-fluoresce under ultraviolet or near-ultraviolet light and which can, at least temporarily, bind to chitin which is a major constituent of the exoskeleton of arthropod ectoparasites and their eggs. The selected dye can be incorporated into a shampoo or a rinsing solution and is applied to the scalp or other desired region of the host patient. After a suitable period of time has elapsed, the dye-containing solution or shampoo is rinsed off and the hair and adjacent area examined under an ultraviolet or a near-ultraviolet light. For example, the detection light can be a Wood's lamp or an incandescent lamp filtered with a cobalt blue filter. Such illumination will cause the stained ectoparasites and/or eggs to glow and, thus, become easily detectable for diagnosis and subsequent removal treatment. The method of the present invention may be applied to detect scabies (i.e. skin-burrowing mites), head lice, body and pubic lice and to any other arthropod ectoparasites and their eggs which are constituted in a substantial part by chitin.

Numerous other advantages and features of the present invention will become apparent to those of ordinary skill in the art from the following detailed description of the invention, from the claims and from the accompanying drawing.

BRIEF DESCRIPTION OF THE DRAWING

The preferred embodiment of the present invention will be described below with reference to the accompanying drawing wherein.

DESCRIPTION OF THE PREFERRED EMBODIMENT

Figure 1:
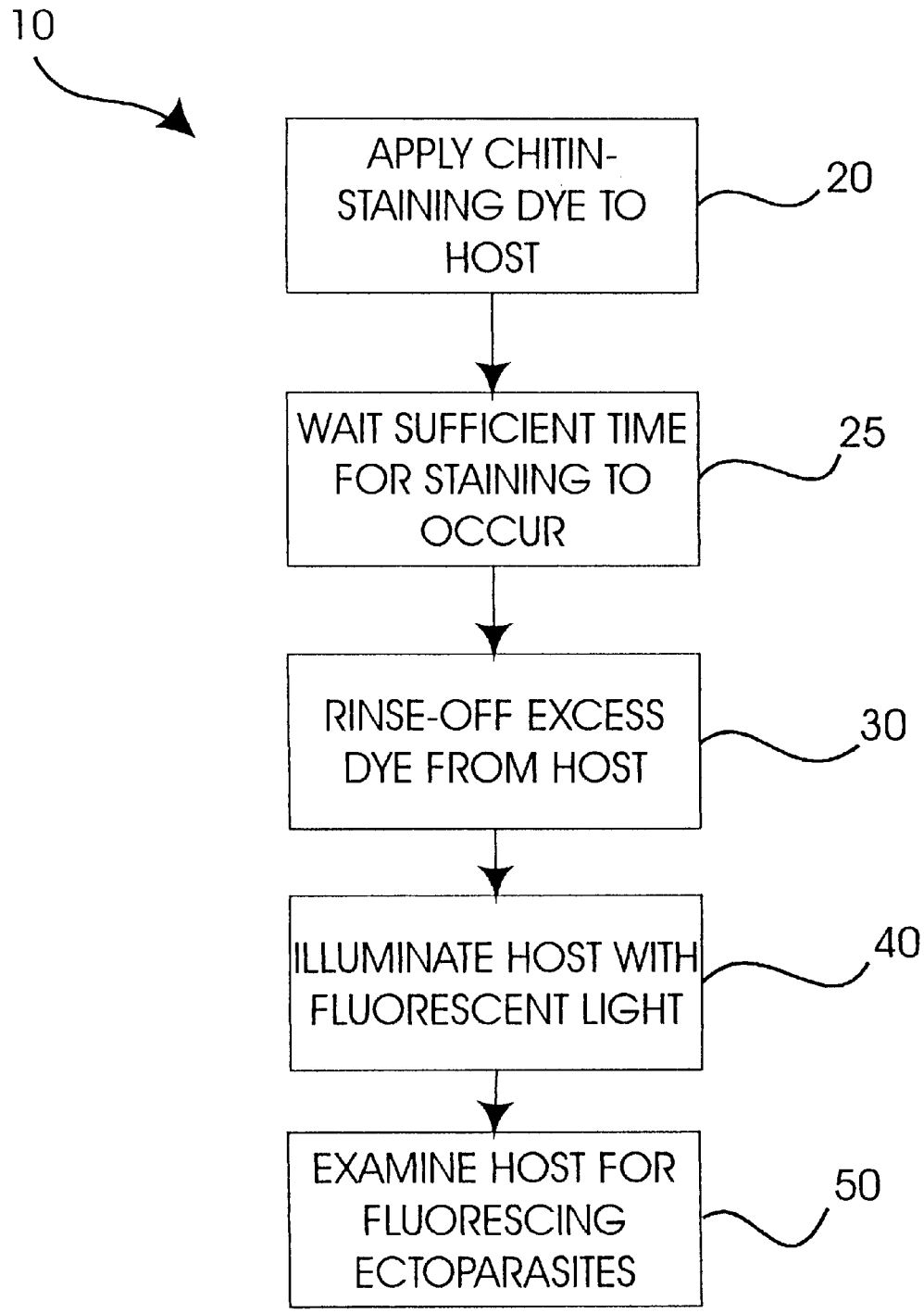
FIG. 1 is a block diagram illustrating the preferred method of the present invention.

The preferred embodiment of the present invention is directed to the detection of infestation in humans by head lice, i.e., pediculosis capitis, but may also have application in connection with the detection of other arthropods such as scabies which are mites. With reference to the accompanying FIG. 1, a diagram illustrating the method is designated by the numeral 10. The preferred embodiment employs a fluorescent dye which stains any ectoparasites and/or their eggs infesting a host when a solution containing the dye is applied to the host as shown in block 20.

One suitable dye is Calcofluor White M2R™ formerly manufactured by American Cyanamid. Calcofluor White M2R™ dye is a fluorochrome dye identified as a "C. I. Fluorescent Brightener 28". The chemical name for this fluorescent dye is believed to be the disodium salt of 4,4'-bis-[4-anilino-bis-(beta-hydroxyethyl) amino-s-triazin-2-ylamino]-2,2'-stilbene-disulfonic acid. Since Calcofluor White M2R™ dye readily binds to chitin, and since chitin is a major constituent of arthropod ectoparasite exoskeletons, it readily stains such arthropod ectoparasites. However, the Calcofluor White M2R™ dye will not stain the host's hair and/or skin in the immediate vicinity of the infestation due to a lack of chitin in the host's hair and skin. The Calcofluor White M2R™ dye is preferably diluted to form a one percent aqueous solution which can be applied to the host. Alternatively, the Calcofluor White M2R™ dye can be incorporated into a shampoo to be applied to the host patient. The concentration of Calcofluor White M2R™ dye in the shampoo may be on the order of one percent (weight per volume).

Alternatively, the dye can be any one of a wide variety of dyes which self-fluoresce under ultraviolet light and which can, at least temporarily, bind to chitin. One suitable fluorescent dye is Blankophor SOL™ fluorescent dye identified as "Benzo Pyranone Optical Brightener" and manufactured by Bayer Corporation. The chemical name is believed to be 2H-1-benzopyran-2-one, 7-(diethylamino)-4-methyl.

Another suitable fluorescent dye is Uvitex 3BSA™ fluorescent dye identified as belonging to the "Triazinyl Stilbene" chemical family and manufactured by Ciba-Geigy Corporation. The chemical name is believed to be [2,2-(2, 5-thiophenidyl)bis-(5-tert-butylbenzoxazole)]. Uvitex 3BSA™ fluorescent dye is believed to be a 15.5% solution of a solid form of Uvitex 2B™ material.

Another suitable fluorescent dye is Rylux BSU™ fluorescent dye manufactured by Ostacolor a.s., of Pardubice-Rybitvi, Czech Republic. Chemically, Rylux BSU™ is believed to be the hexasodium salt of 1,4-benzenedisulfonic acid 2,2'-[ethyleneidyl bis(3-sulpho-4,1-phenylene)imino [6-bis(2-hydroxyethyl)amino]1,3,5-triazine 4,2-diacylamino].

For example, an alternative embodiment of the present invention may employ Blankophor™, Uvitex™ or Rylux BSU™ dye as a substitute for the Calcofluor White M2R™ dye as the fluorescent dye.

After the fluorescent dye solution has been applied to the host, the dye-containing solution should be afforded ample time to bind with the chitin of the ectoparasites and/or their eggs. This time period (see block 25 of FIG. 1) preferably varies between ten seconds and ten minutes. After sufficient time has elapsed, the dye-containing solution is rinsed off of the host as shown in block 30 of FIG. 1.

The hair and adjacent area of the host can then be examined under an ultraviolet or a near-ultraviolet light (blocks 40 and 50 of FIG. 1). Naturally, the efficacy of examining a region of dense hair can be improved by tousling the patient's hair to expose the lower portion of the hair shafts and underlying skin. The detection light is preferably either a Wood's lamp or an incandescent lamp filtered with a cobalt blue filter. Additionally, a variety of well-known lamps which produce ultraviolet or near-ultraviolet light can also be utilized. Regardless of the source, however, such illumination will cause the stained ectoparasites and/or ectoparasite eggs to glow bluish-white in color and, thus, become easily detectable for diagnosis and subsequent removal.

Removal can be achieved by hand removal of the ectoparasites, by the use of a conventional fine tooth comb. However, since the ectoparasites are now fluorescent, the conventional methods of treating infestations can be accomplished much more efficiently and accurately. In addition to verifying a preliminary and speculative diagnosis that ectoparasite infestation has occurred, the present invention can be utilized as a periodic prophylactic test for ectoparasite detection. Thus, by administering the method of the present invention on a regular basis, it becomes possible to detect and treat infestations before they reach a severe level. The method provides an efficient and reliable method for inspection for lice infestation of a large number of children.

This embodiment of the present invention is primarily directed to detecting head lice. However, scabies, body lice, pubic lice and any other arthropod ectoparasites containing a substantial percentage of chitin in their exoskeletons can also be detected with minor modifications.

TEST EXAMPLE I

A nit attached to a hair shaft, obtained from a patient infested with head lice, was examined under the light of a Wood's lamp. Neither the nit nor the hair shaft fluoresced. The nit was then immersed in an approximately one percent (weight per volume) aqueous solution of Calcofluor White M2R™ dye for one minute, rinsed in water, and reexamined under the Wood's lamp. The nit, but not the hair shaft, emitted a blue-white fluorescence. The nit was re-immersed in the same staining solution for five additional minutes, rinsed in water once again, and again examined under the Wood's lamp. Again, the nit fluoresced (slightly more intensely), but the hair shaft did not.

TEST EXAMPLE II

The procedure of Example 1 was repeated using a fresh, unstained nit obtained from the same source as the first. This time, the nit was immersed in the Calcofluor White M2R™ staining solution only once, for two minutes. Once again, the nit glowed blue-white under the Wood's lamp. The intensity of the glow was approximately the same as the intensity of the glow noted in the first test.

TEST EXAMPLE III

A nit attached to a hair shaft, obtained from a patient infested with head lice, was examined under the light of a Wood's lamp. Neither the nit nor the hair shaft fluoresced. The nit was then immersed in a 1% (weight per volume) solution of Blankophor SOL™ (Bayer Corporation, Industrial Chemicals Division, lot 50-70-806) dye in TRESemmé Deep Cleansing Shampoo™ (Alberto-Culver) for one minute, rinsed in water, and reexamined under the Wood's lamp. The nit, but not the hair shaft, emitted a bright blue-white fluorescence.

TEST EXAMPLE IV

The experiment of Example III was then repeated, staining the nit with a 0.5% (weight per volume) solution of Blankophor SOL™ dye in shampoo and limiting the immersion time in the dye solution to 15 seconds. Again, the stained nit emitted a blue-white fluorescence under Wood's lamp illumination and under illumination with a small incandescent bulb fitted with cobalt-blue filter.

TEST EXAMPLE V

A similar procedure was repeated using a fresh, unstained nit obtained from the same source as Example III. This time, the nit was immersed in a 1% (weight per volume) solution of Uvitex 3BSA™ (Ciba-Geigy Corporation, Chemicals Division, batch 6568) dye in TRESemmé Deep Cleansing Shampoo™ (Alberto-Culver) for one minute, rinsed in water, and reexamined under the Wood's lamp. Again, the nit glowed blue-white under the Wood's lamp. The intensity of the glow was even brighter than the glow noted of the nit stained with 1% Blankophor SOL™ dye of Example III.

A table summarizing various dye concentrations and staining times is presented below:

| dye | concentration | medium | staining time |
| --- | --- | --- | --- |
| Calcofluor White M2R™ | 1% (w/v) | water | 1–5 minutes |
| Blankophor SOL™ | 1% (w/v) | shampoo | 1 minute |
| Blankophor SOL™ | 0.5% (w/v) | shampoo | 15 seconds |
| Uvitex 3BSA™ | 1% (w/v) | shampoo | 1 minute |

For each of the table entries, positive nit detection was achieved by fluorescence detection.

Preferably the concentration of dye in shampoo is in the range of approximately 0.25 to 5% weight per volume. Preferably the step of applying the solution is in the approximate range of ten seconds to ten minutes.

This detection method, which is applicable to the identification of nits in patients infested with head lice, shows that a variety of chitin-staining fluorescent dyes may be used for this purpose, that such dyes may be incorporated into a shampoo preparation, and that the light source used to excite the fluorescence of the chitin-binding stain may be a Wood's lamp or may be a cobalt-blue filtered incandescent source.

While the present invention has been described in connection with what is presently considered to be the preferred embodiments, it is to be understood that the invention is not limited to the disclosed embodiments but is intended to cover various modifications and equivalent arrangements included within the spirit and scope of the appended claims.

What is claimed is:

1. A method of detecting arthropod ectoparasites and/or arthropod ectoparasite eggs while the ectoparasites and/or eggs are infesting a host, said method comprising:
    a) applying a dye solution to a host suspected of being infested with arthropod ectoparasites and/or arthropod ectoparasite eggs, said solution comprising a chitin-binding dye which fluoresces under fluorescence-exciting light, under conditions sufficient to bind at least some of the dye in the applied solution to any said ectoparasites and eggs present on the host and thereby stain any said ectoparasites and eggs but not tissues of the host;
    b) rinsing the solution from the host so as to substantially remove the dye from the host but selectively allow at least some of the dye to remain bound to any said stained ectoparasites and eggs;
    c) illuminating the host with fluorescence-exciting light in order to illuminate any said stained ectoparasites and eggs and thereby cause the dye bound thereto to visibly fluoresce; and
    d) examining said illuminated host wherein the presence of visibly fluorescing stained ectoparasites and/or visibly fluorescing stained eggs indicates arthropod ectoparasite infestation of the host.

2. The method of claim 1, wherein said step of illuminating includes subjecting the host, stained ectoparasites and stained eggs to low-frequency ultraviolet light.

3. The method of claim 1, wherein said step of illuminating includes subjecting the host, stained ectoparasites and stained eggs to a near-ultraviolet light.

4. The method of claim 1, wherein said step of applying further comprises incorporating the dye into a shampoo and washing at least a portion of the host with the shampoo.

5. The method of claim 4 wherein the concentration of dye in the shampoo is approximately 0.25% to 5.0%, weight/volume.

6. The method of claim 1, wherein said step of applying includes exposing the host, ectoparasites and ectoparasite eggs to a dye solution for at least approximately 10 seconds.

7. The method of claim 1, wherein said step of applying includes exposing the host, ectoparasites and ectoparasite eggs to a dye solution for no more than approximately 10 minutes.

8. The method of claim 1, wherein said step of applying includes exposing the host, ectoparasites and eggs to a dye solution containing approximately 0.25% to 5.0%, weight/volume, dye.

9. The method of claim 1, wherein said step of illuminating includes subjecting the host, stained ectoparasites and stained eggs to light emitted from a Wood's lamp.

10. The method of claim 1, wherein the ectoparasites comprise scabies and wherein the ectoparasite eggs comprise scabie eggs.

11. A method of detecting arthropod ectoparasite eggs affixed to a host, said method comprising:
    (a) washing the host suspected of being infested with arthropod ectoparasite eggs with a solution containing a chitin-binding dye which fluoresces under a fluorescence-exciting light, said washing lasting for a predetermined time sufficient to stain the eggs but not tissues of the host;
    (b) rinsing the solution from the host so as to substantially remove the dye from the host but selectively allow at least some of the dye to remain bound to any said stained arthropod ectoparasite eggs;
    (c) illuminating the host with fluorescence-exciting light in order to illuminate any said stained arthropod ectoparasite eggs and thereby cause the dye bound thereto to visibly fluoresce; and
    (d) examining said illuminated host wherein the presence of visibly fluorescing stained eggs indicates arthropod egg infestation of the host.

12. The method of claim 11, wherein said step of illuminating the host and eggs with fluorescence-exciting light comprises subjecting the host and eggs to low-frequency ultraviolet light.

13. The method of claim 11, wherein said step of illuminating the host and eggs with fluorescence-exciting light comprises subjecting the host and eggs to near-ultraviolet light.

14. The method of claim 11 wherein step of washing is performed for a time interval that ranges from approximately 10 seconds to 10 minutes.

15. The method of claim 11, wherein said step of illuminating comprises exposing the host and eggs to light emitted from a Wood's lamp whereby the eggs visibly fluoresce.

16. The method of claim 11, wherein said step of washing includes exposing the host, ectoparasites and ectoparasite eggs to an approximately one percent, weight/volume aqueous solution of fluorescent dye for at least approximately one minute.

17. The method of claim 11 further comprising mixing a dye with shampoo to form the solution.

18. A method of detecting arthropod ectoparasites and/or arthropod ectoparasite eggs while the ectoparasites and/or eggs are infesting a host, said method comprising:
    a) applying a solution comprising a shampoo and a dye to a host suspected of being infested with arthropod ectoparasites and/or arthropod ectoparasite eggs, said dye comprising a chitin-binding dye which fluoresces under fluorescence-exciting light, under conditions sufficient to bind at least some of the dye in the applied solution to any said ectoparasites and eggs present on the host and thereby stain any said ectoparasites and eggs but not tissues of the host;

b) rinsing the solution from the host so as to substantially remove the shampoo and dye from the host but selectively allow at least some of the dye to remain bound to any said stained ectoparasites and eggs;

c) illuminating the host with fluorescence-exciting light in order to illuminate any said stained ectoparasites and eggs and thereby cause the dye bound thereto to visibly fluoresce; and d) examining said illuminated host wherein the presence of visibly fluorescing stained ectoparasites and/or visibly fluorescing stained eggs indicates arthropod ectoparasite infestation of the host.

* * * * *